(12) United States Patent
Miyata

(10) Patent No.: US 6,383,355 B1
(45) Date of Patent: May 7, 2002

(54) GAS SENSOR

(75) Inventor: Hiroshi Miyata, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/597,152

(22) Filed: Jun. 20, 2000

(30) Foreign Application Priority Data

Jun. 21, 1999 (JP) .......................................... 11-174257

(51) Int. Cl.⁷ ............................................ G01N 27/407
(52) U.S. Cl. ...................................... 204/427; 204/428
(58) Field of Search ................................ 204/421–429

(56) References Cited

U.S. PATENT DOCUMENTS

| | | | |
|---|---|---|---|
| 4,141,813 A | * | 2/1979 | Kita et al. |
| 4,362,609 A | | 12/1982 | Sano et al. |
| 4,786,399 A | | 11/1988 | Wertheimer et al. |
| 5,785,829 A | | 7/1998 | Watanabe |
| 6,018,982 A | | 2/2000 | Friese et al. |
| 6,039,856 A | | 3/2000 | Weyl et al. |

FOREIGN PATENT DOCUMENTS

| | | |
|---|---|---|
| JP | 10-83843 | 3/1998 |
| JP | 10-300714 | 11/1998 |
| JP | 2000-503399 | 3/2000 |

OTHER PUBLICATIONS

European Search Report dated Oct. 19, 2000 for EP 00 30 5200.

* cited by examiner

Primary Examiner—T. Tung
(74) Attorney, Agent, or Firm—Sughrue Mion, PLLC

(57) ABSTRACT

A gas sensor having improved heat resistance and oil resistance. A portion of a cylindrical cover attached to a metallic shell 29 is formed of a bendable resin tube 50. When the sensor is installed in a location susceptible to oil splashes, a rubber member 54 having intercommunicating holes 58 formed therein can be moved to a position where the rubber member 54 is less susceptible to oil splashes, through appropriate bending of the resin tube 50. Thus, entry of oil into the interior of the sensor is avoided. Also, since the resin tube 50 is bendable, the length of the resin tube 50 can be increased so long as an ambient space around the installed sensor permits, thereby decreasing heat transmitted from the metallic shell 29 to the rubber member 54.

8 Claims, 3 Drawing Sheets

GAS SENSOR

BACKGROUND OF THE INVENTION

1. Field of the Invention

The present invention relates to a gas sensor installed in a flow path through which flows a gas to be measured, such as an exhaust gas, the gas sensor functioning while introducing reference air into the gas sensor from its exterior.

2. Description of the Related Art

Conventionally known gas sensors for determining the concentration of a specific gas component in a mixed gas include HC sensors and NOx sensors. An example of such a gas sensor is an oxygen sensor as shown in FIG. 3 of the accompanying drawings. The oxygen sensor includes a detection element S, which, in turn, includes an oxygen-ion-conductive solid electrolyte body.

The detection element S includes an element body 503, which is a closed-bottomed cylindrical solid electrolyte body which is closed at one end and opened at the other end; an internal electrode 505 formed on the inner surface of the element body 503; and an external electrode 507 formed on the outer surface of the element body 503. An electromotive force is generated between the internal and external electrodes 505 and 507 according to the difference in oxygen concentration between the internal space of the detection element S and the exterior of the detection element S. For example, when the closed end of the detection element S is projected via a metallic shell 509 into the interior of the exhaust pipe of an internal combustion engine to thereby expose the external electrode 507 to an exhaust gas, the oxygen concentration in the exhaust gas can be determined from an electromotive force generated between the internal and external electrodes 505 and 507.

In order to accurately measure the oxygen concentration in a gas being measured, a reference oxygen concentration on the side of the internal electrode 505 must be maintained constant. Thus, for example, air is introduced into the interior of the oxygen sensor through gaps among strands of a lead wire. However, when foreign matter, such as water, enters the internal space of the detection element S, the oxygen concentration cannot be measured properly.

To cope with this problem, conventionally, as shown in FIG. 3, a cylindrical cover (an internal cylindrical member 511 and an external cylindrical member 513) is attached to the upper opening (i.e., the opening located outside the flow path) of the metallic shell 509 so as to cover an upper portion of the detection element S. Also, a rubber member 515 is disposed at an exit portion of the cylindrical cover for lead wires connected to the internal and external electrodes 505 and 507 in order to prevent foreign matter, such as water, from entering the internal space of the detection element S.

In spite of employing of the above-mentioned waterproofing measures, entry of the gas being measured from the flow path or capillarity-effected entry of liquid (for example, water or oil) through gaps among strands of a lead wire cannot be prevented completely. A gas generated through vaporization of liquid which has entered, or a gas being measured which has entered may cause a change in the oxygen concentration within the oxygen sensor, thus affecting the results of the measurement. To cope with this problem, for example, a gas-permeable water-repellent filter 517 of a fluorine-containing resin is disposed to cover intercommunicating holes 519 and 521 formed in the wall of the cylindrical cover, whereby a gas which may cause measurement error is ejected therethrough, and air is introduced therethrough into the oxygen sensor, to thereby measure the oxygen concentration accurately.

When the above-mentioned oxygen sensor is used for determining the oxygen concentration in a high-temperature exhaust gas, the oxygen sensor is placed in a high-temperature environment. Thus, the metallic shell 509, which is attached to an exhaust pipe while holding the detection element S, and the internal and external cylindrical members 511 and 513, which are adapted to supply air to the internal electrode 505, are formed from a metal (for example, stainless steel).

However, the rubber member 515 and the water-repellent filter 517 are low in critical heat-resistant temperature as compared with a refractory metal. Thus, long-term use at high temperature has occasionally involved the following phenomena: the elasticity of the rubber member 515 deteriorates, thereby causing an impairment in waterproofing; and the water-repellent filter 517 is thermally deformed, thereby causing blockage of holes with a resultant impairment in gas permeability.

When the oxygen sensor is attached to the exhaust pipe of a car, a certain position of attachment may involve splashing the oxygen sensor with engine oil. In this case, oil may enter the interior of the oxygen sensor through the water-repellent filter 517, thereby impairing the function of the oxygen sensor or impairing the gas permeability of the water-repellent filter 517 with a resultant difficulty in introducing air in a favorable manner.

The above-mentioned problems arise with not only an oxygen sensor but also other gas sensors which require waterproofing and introduction of air, such as NOx sensors and HC sensors.

SUMMARY OF THE INVENTION

The present invention has been accomplished in view of the above-mentioned problems, and an object of the present invention is to improve the heat resistance and oil resistance of a gas sensor.

Accordingly, a gas sensor of the present invention is characterized as comprising: a detection element comprising an oxygen-ion-conductive solid electrolyte body and electrodes formed on the solid electrolyte body; a metallic shell formed so as to be attachable in a mounting hole formed in a wall of a flow path through which flows a gas to be measured, and adapted to hold the detection element; a cylindrical cover disposed opposite the flow path with respect to the metallic shell and adapted to introduce air to one of the electrodes formed on the solid electrolyte body, within which lead wires electrically connected to the electrodes of the detection element are disposed and at least a portion of which is bendable; an elastic member having an intercommunicating hole formed therein through which air is introduced into the interior of the cylindrical cover, and having through-holes formed therein through which the lead wires extend; and a water-repellent filter having gas permeability and positioned such that air to be introduced into the interior of the cylindrical cover through the intercommunicating hole formed in the elastic member passes therethrough.

In the gas sensor of the present invention having the above-mentioned structure, the cylindrical cover is disposed opposite the flow path with respect to the metallic shell which holds the detection element. The elastic member for waterproofing is disposed at an opening portion of the cylindrical cover located opposite the metallic shell. The elastic member has through-holes formed therein. The lead wires extend to the exterior of the gas sensor through the through-holes. Also, the elastic member has formed therein the intercommunicating hole through which air is introduced into the interior of the cylindrical cover. The water-repellent filter is disposed such that air to be introduced into the cylindrical cover through the intercommunicating hole passes therethrough. These structural features enable introduction of air into the interior of the cylindrical cover and prevent entry of water into the same.

Particularly, in the present invention, at least a portion of the cylindrical cover is bendable. By bending the bendable portion, the position of the elastic member can be changed.

Thus, when the gas sensor of the present invention is installed where the gas sensor is potentially susceptible to oil splashes, the elastic member having the intercommunicating hole formed therein can be moved to such a position at which the elastic member is less susceptible to oil splashes, through bending and straightening the cylindrical tube.

Accordingly, the possibility of entry of oil into the gas sensor, which causes a detection error, or the possibility of adhesion of oil to the water-repellent filter, which hinders gas flow through the intercommunicating hole (introduction of air from outside the gas sensor or ejection of the exhaust gas which has entered the interior of the gas sensor), can be reduced.

According to the gas sensor of the present invention, the cylindrical cover is bendable, so that the cylindrical cover can be disposed along the route of the lead wires. Specifically, the length of the cylindrical cover can be increased so long as an ambient space of the installed gas sensor permits. Thus, in the case where the gas sensor is attached to an exhaust pipe, heat transmitted from the metallic shell to the elastic member through the cylindrical cover can be decreased. Also, the elastic member can be moved to a position less exposed to radiant heat from the exhaust pipe. As a result, a temperature rise of the elastic member and the water-repellent filter can be suppressed, thereby extending their service lives and thus extending the service life of the gas sensor.

When the gas sensor is used to determine the concentration of a target component in a high-temperature exhaust gas, the temperature of the metallic shell used to attach the gas sensor to an exhaust pipe, through which the exhaust gas flows, becomes high. Thus, the temperature of the cylindrical cover attached to the metallic shell also becomes high in the vicinity of the metallic shell.

To cope with the above problem, advantageously, the cylindrical cover may comprise a first cover formed from a metal and disposed opposite the flow path with respect to the metallic shell; and a second cover being bendable and disposed opposite the metallic shell with respect to the first cover.

According to the gas sensor having this structure, a portion of the cylindrical cover located in the vicinity of the metallic shell is composed of the first cover of a metal, thereby improving the heat resistance of the cylindrical cover.

In the above preferred gas sensor, the bendable second cover disposed opposite the metallic shell with respect to the first cover may assume the form of cylindrical bellows made of a metal, thereby reliably protecting the lead wires accommodated therein. However, when the first and second covers are of a metal, the gas sensor may become too heavy, potentially causing inconvenience in handling. Also, when the first cover and the second cover differ in coefficient of thermal expansion, the connection of the first and second covers may involve difficulty in maintaining good sealing performance.

To cope with the above problem, preferably, the second cover may be formed from an elastic, heat-resistant resin or rubber.

According to the gas sensor having this structure, the second cover is formed from a resin or rubber, so that the total weight of the oxygen sensor can be decreased as compared to the case where the second cover is formed from a metal. Also, the elasticity of the second cover facilitates maintenance of a seal at a connection with the first cover, thereby yielding a waterproofing effect. Since a resin or rubber is poorer in thermal conductivity than a metal, a temperature rise of the elastic member and the water-repellent filter can be further suppressed. Examples of an elastic, heat-resistant resin include PTFE resins, such as Teflon (trade name), and PFA resins. The second cover of a fluorine-containing resin exhibits excellent heat resistance and oil resistance and is thus preferred. Specific examples of rubber include silicone rubber, EPDM rubber, and composite rubber of silicone rubber and other rubber material.

The water-repellent filter may assume the form of a hard, porous foamed body of a PTFE resin inserted into the intercommunicating hole formed in the elastic member. However, this form is disadvantageous in terms of intercommunicating performance.

To cope with this problem, preferably, the water-repellent filter may assume the form of a sheet and may be disposed so as to cover an opening of the intercommunicating hole facing the exterior of the gas sensor.

According to the gas sensor having this structure, the water-repellent filter assumes the form of a sheet, so that good intercommunication is established; specifically, air can be smoothly introduced into the interior of the gas sensor, and an exhaust gas which has entered the interior of the gas sensor can be smoothly ejected to the exterior of the gas sensor.

BRIEF DESCRIPTION OF THE DRAWINGS

FIG. 2(*b*) is a sectional view taken along line α—α of (*a*).

Figure 1:
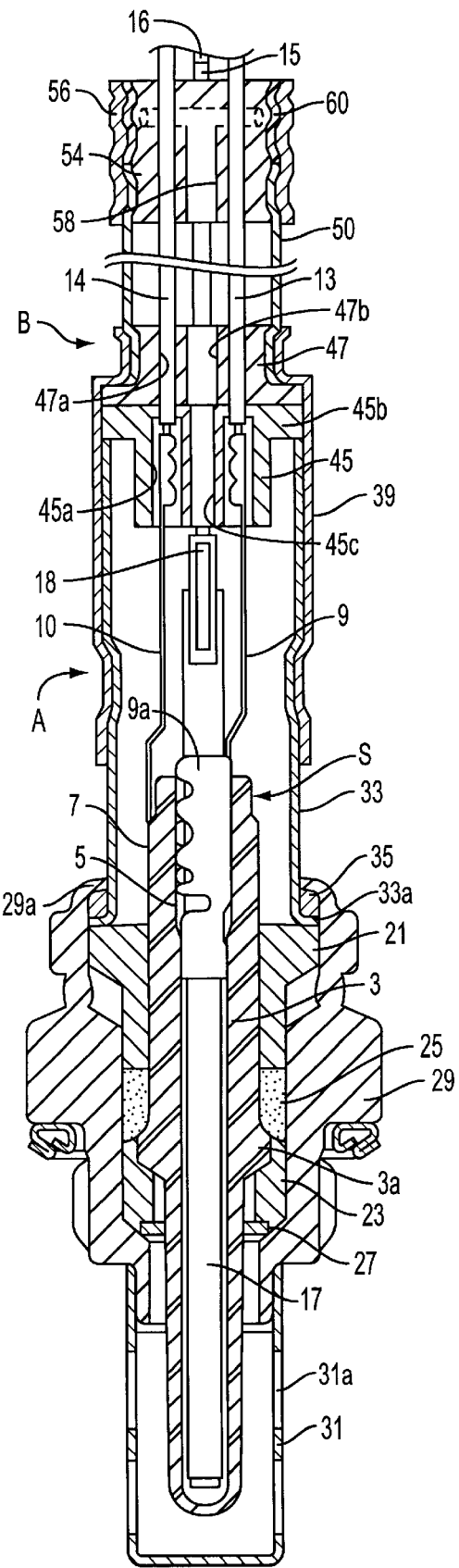
FIG. 1 is a sectional view showing the entire structure of an oxygen sensor according to an embodiment of the present invention.

Reference numerals are used to identify items shown in the drawings as follows:
3: detection element body
5: internal electrode
7: external electrode
13–16: lead wires
29: metallic shell
33: internal cylindrical member (first cover)
39: external cylindrical member (first cover)
50: resin tube (second cover)
54: rubber member (elastic member)
54*a*: through-hole
58: intercommunicating hole
58*a*: side opening
60: water-repellent filter
S: detection element

DESCRIPTION OF THE PREFERRED EMBODIMENTS

An embodiment of a gas sensor of the present invention will next be described with reference to the drawings.

However, the present invention should not be construed as being limited thereto.

FIG. 1 is a sectional view showing the entire structure of an oxygen sensor according to the embodiment. The oxygen sensor includes a sensor body composed of a detection element S for detecting oxygen concentration; a metallic shell 29 to be attached to a flow path of a gas to be measured while holding the detection element S; and an internal cylindrical member 33 and an external cylindrical member 39 extending from an upper opening of the metallic shell 29 (i.e., an opening located opposite the flow path). The internal and external cylindrical members 33 and 39 correspond to the "first cover."

In this oxygen sensor, the detection element S for detecting oxygen concentration includes a detection element body 3 as shown in FIG. 1. The detection element body 3 is an oxygen-ion-conductive solid electrolyte body which contains a predominant amount of zirconia and which assumes the form of a closed-bottomed cylinder, which is closed at one end and opened at the other end. An internal electrode 5 and an external electrode 7 are formed on the inner and outer surfaces, respectively, of the detection element body 3. Each of the internal and external electrodes 5 and 7 is a heat-resistant, porous electrode of platinum. An outer central portion of the detection element body 3 is formed into a flange portion 3a. Lead wires 13 and 14 (covered for protection) are connected via output terminals 9 and 10 to the inner and outer surfaces, respectively, of an opening portion of the detection element S for outputting therethrough signals emitted from the internal and external electrodes 5 and 7.

The output terminal 9 is fitted into the opening portion of the detection element S to thereby be electrically connected to the internal electrode 5. The output terminal 9 has a heater holder portion 9a at its lower end (an end located at the near side with respect to the closed end of the detection element body 3) for holding a ceramic heater 17 adapted to activate the detection element S through application of heat. The rod-like ceramic heater 17 is held at its outer circumferential portion by the heater holder portion 9a, thereby being disposed within the internal space of the detection element S. The ceramic heater 17 has a pair of electrodes formed on its surface, to which a pair of lead terminals 18 are brazed. Lead wires 15 and 16 are connected to the ceramic heater 17 via the corresponding lead terminals 18 for supplying electricity to the ceramic heater 17. Being electrically energized through the lead wires 15 and 16, the ceramic heater 17 generates heat to thereby activate the detection element S through application of heat.

The detection element S is disposed within the metallic shell 29 of a refractory metal by means of, in the ascending order, a packing 27, a cylindrical, lower holding member 23 of ceramic, a talc powder 25, and a cylindrical, upper holding member 21 of ceramic. The detection element S is disposed within the metallic shell 29 in such a manner as to be coaxial with the metallic shell 29 and to extend through the metallic shell 29 in a vertical direction in the drawing. Since a lower end portion (i.e., a closed-end portion) of the thus-disposed detection element S projects from a lower portion of the metallic shell 29, a protection cap 31 is attached to the lower portion of the metallic shell 29 so as to cover the end of the detection element S. The protection cap 31 has hole portions 31a for introducing thereinto a gas to be measured.

The internal cylindrical member 33 of a refractory metal (stainless steel in the present embodiment) is attached to an upper portion of the metallic shell 29 through caulking while an O ring 35 is held therebetween, in such a manner as to enclose upper portions of the detection element S and the ceramic heater 17. Specifically, an internal-cylindrical-member flange portion 33a formed at a lower end portion of the internal cylindrical member 33 is disposed above the upper holding member 21. The O ring 35 is disposed above the internal-cylindrical-member flange portion 33a. In this state, an edge portion 29a of the upper end of the metallic shell 29 is caulked in such a manner as to be bent inward and compressed downward while covering the O ring 35. Thus, the internal cylindrical member 33 is attached to the upper opening of the metallic shell 29 while airtightness is established at a connection portion between the metallic shell 29 and the internal cylindrical member 33.

A substantially columnar separator 45 of ceramic is disposed at an upper portion of the internal cylindrical member 33 and has through-holes 45a formed therein. The lead wires 13–16, and the output terminals 9 and 10 and the lead terminals 18 connected to the lead wires 13–16 extend axially through the corresponding through-holes 45a. A separator flange portion 45b formed at an upper portion of the separator 45 is engaged with the upper end of the internal cylindrical member 33, whereby the separator 45 is held at an upper portion of the internal cylindrical member 33. A substantially columnar resin member 47 of a fluorine-containing resin (e.g., TEFLON (trade name) in the present embodiment) is disposed on the separator 45. The resin member 47 has through-holes 47a formed therein. The lead wires 13–16 extend axially through the through-holes 47a. Thus, the internal cylindrical member 33, the separator 45, and the resin member 47, in the ascending order, are disposed above the metallic shell 29.

The external cylindrical member 39 of a refractory metal (stainless steel in the present embodiment) is fitted to the thus-disposed internal cylindrical member 33, the separator 45, and the resin member 47 in such a manner as to cover their side surfaces. The external cylindrical member 39 is radially caulked at position A where the external cylindrical member 39 overlaps the outer circumferential surface of the internal cylindrical member 33, and at position B where the external cylindrical member 39 overlaps the outer circumferential surface of the resin member 47. As a result, the external cylindrical member 39 is fixedly attached to the internal cylindrical member 33. Also, the separator 45 and the resin member 47 are fixedly disposed on an upper portion of the internal cylindrical member 33 by means of the external cylindrical member 39.

Figure 2A:
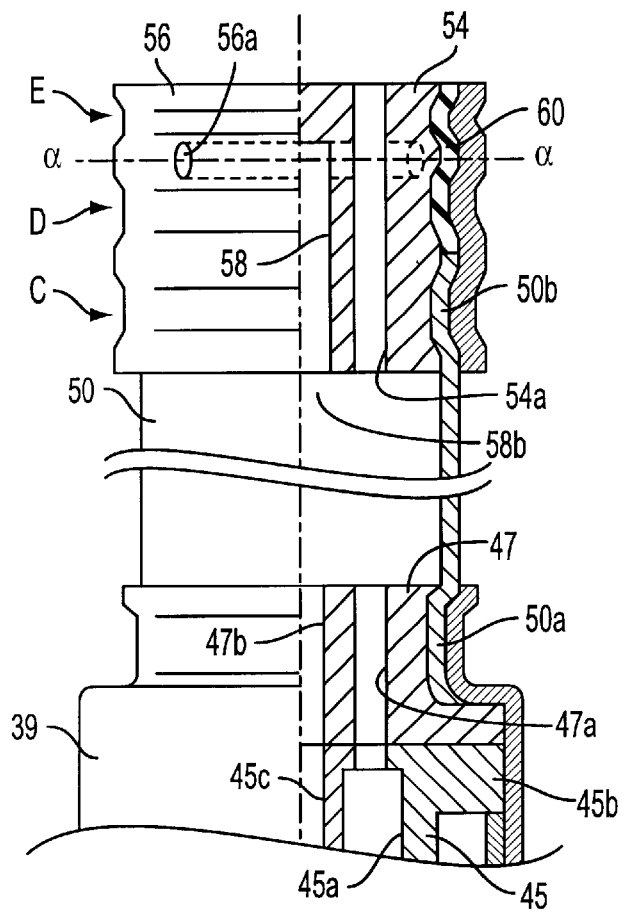
FIG. 2(*a*) is a detailed sectional view showing a harness portion of the oxygen sensor.
Figure 2B:
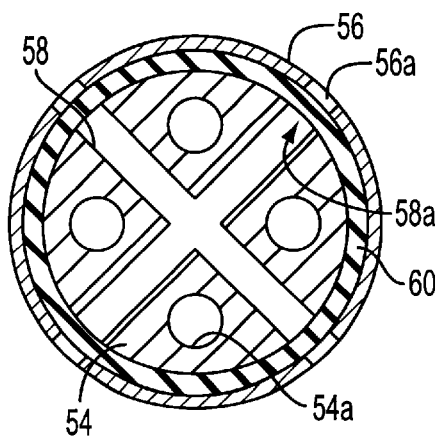
Figure 3:
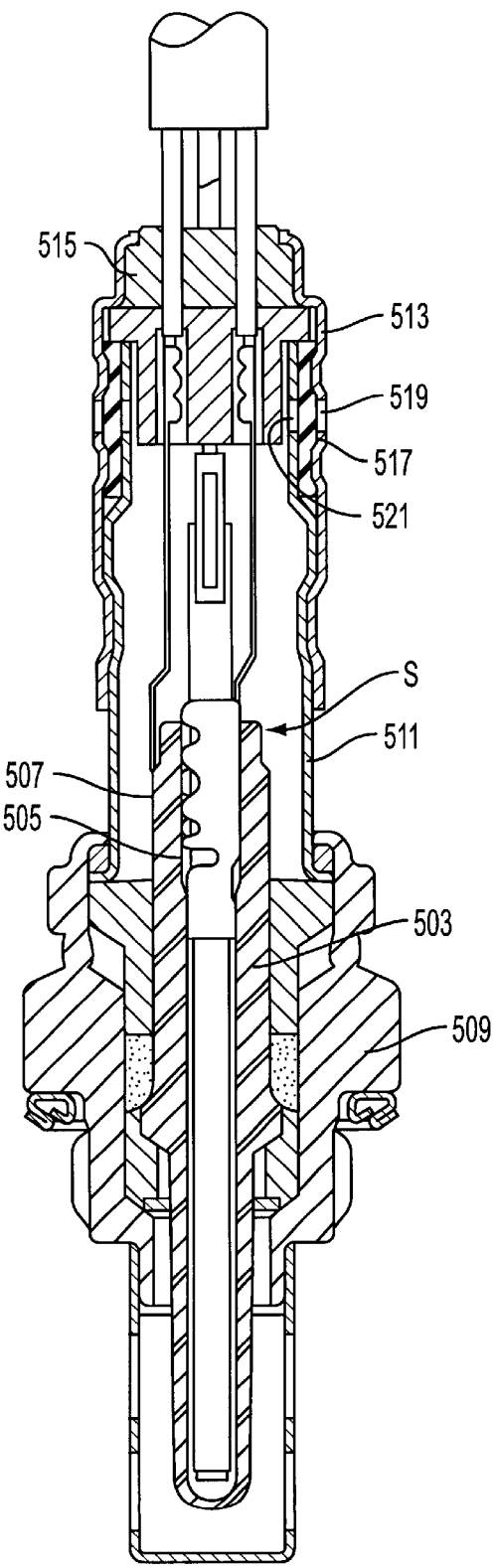
FIG. 3 is a sectional view showing the structure of a conventional oxygen sensor.

As shown in FIGS. 1 and 2, in the oxygen sensor of the present embodiment, a harness portion is attached to an upper portion of the sensor body having the above-described structure (i.e., from an upper portion of the external cylindrical member 39). The harness portion assumes the shape of a cylinder having openings formed at opposite ends thereof. The harness portion includes a resin tube 50 disposed within a hollow portion thereof. The resin tube 50 accommodates the lead wires 13–16. For the sake of simplicity, the lead wires 13–16 and the output terminal 9 do not appear in FIG. 2.

The resin tube 50 corresponds to the "second cover" and is formed from a fluorine-containing resin (e.g., TEFLON (trade name) in the present embodiment). One open end of the resin tube 50 (hereinafter called the "lower open end 50a") is fixedly held between the outer circumferential surface of the resin member 47 and the inner circumferential surface of the external cylindrical member 39. That is, the external cylindrical member 39 is caulked onto the resin member 47 while the lower open end 50a of the resin tube 50 is inserted between the outer circumferential surface of the resin member 47 and the inner circumferential surface of the external cylindrical member 39. Thus, airtightness is established at a connection portion between the external cylindrical member 39 and the resin tube 50.

A rubber member 54 is disposed within an open end of the resin tube 50 located opposite the sensor body (hereinafter called the "upper open end 50b"). The rubber member 54 assumes a columnar form and has through-holes 54a formed therein so that the lead wires 13–16 can axially extend therethrough. That is, the upper open end 50b of the resin tube 50 is fitted onto a lower portion of the rubber member 54. Further, a cylindrical caulking member 56 is fitted onto the thus-engaged portion of the rubber member 54 and the resin tube 50. In this state, the caulking member 56 is radially caulked at a portion under which the rubber member 54 and the resin tube 50 overlap each other (at position C in FIG. 2(a)), thereby fixedly attaching the rubber member 54 to the upper open end 50b of the resin tube 50. The rubber 54 corresponds to the "elastic member."

Intercommunicating holes 58 are formed in the rubber member 54 in such a manner as to extend therethrough to an upper portion of the outer circumferential surface of the rubber member 54 (to thereby form "side openings 58a") and to the lower end face of the rubber member 54 (i.e., the surface of the rubber member 54 which faces the internal space of the resin tube 50) to thereby form openings 58b. An gas-permeable water-repellent filter 60 in the form of a sheet is annularly disposed between the caulking member 56 and an upper portion of the outer circumferential surface of the rubber member 54 (i.e., the water-repellent filter 60 assumes the shape of a cylinder). The side openings 58a are covered by the water-repellent filter 60. The caulking member 56 has openings 56a formed therein at positions corresponding to those of the side openings 58a formed in the rubber member 54. The caulking member 56 is radially caulked at positions above and below the openings 56a (position D and position E in FIG. 2(a)). The side opening 58a corresponds to the "opening facing the exterior of the gas sensor."

Thus, the interior of the resin tube 50 communicates with the exterior of the oxygen sensor only through communicating paths composed of the intercommunicating holes 58 formed in the rubber member 54, the water-repellent filter 60, and the openings 56a formed in the caulking member 56. Communicating paths 45c and 47b are formed in the separator 45 and the resin member 47, respectively, so as to establish communication between the interior of the sensor body and the interior of the resin tube 50. Thus, the internal spaces of the sensor body and the detection element S communicate with the exterior of the oxygen sensor through the caulking member 56, the water-repellent filter 60, the rubber member 54, the resin tube 50, etc.

The oxygen sensor having the above-described structure is attached to, for example, an exhaust pipe of a car engine such that an end portion of the detection element S protected by the protection cap 31 projects into the interior of the exhaust pipe so as to be exposed to an exhaust gas to be measured. The resin tube 50 is brought into a bent or straight state so as to bring the rubber member 54 to a position less susceptible to mud, water, or oil splashes. Air is introduced into the interior of the detection element S through the caulking member 56, the water-repellent filter 60, the rubber member 54, the resin tube 50, etc. As a result, a voltage is generated between the internal electrode 5 and the external electrode 7 of the detection element S according to the ratio between the oxygen concentration in air and the oxygen concentration in the gas being measured. The voltage is output to the exterior of the oxygen sensor in the form of a detection signal.

If the exhaust gas should enter the interior of the sensor body, the exhaust gas is ejected through an exhaust path composed of the resin tube 50, the rubber member 54, the water-repellent filter 60, and the caulking member 56.

According to the oxygen sensor of the present embodiment having the above-described structure, the bendable resin tube 50 serves as a portion of the cylindrical cover attached to the metallic shell 29. Thus, when the oxygen sensor is installed where the oxygen sensor is potentially susceptible to oil splashes, the rubber member 54 having the intercommunicating holes 58 formed therein can be moved to such a position where the rubber member 54 is less susceptible to oil splashes, by bending the resin tube 50. Accordingly, the possibility of entry of oil into the oxygen sensor, which causes a detection error, or the possibility of adhesion of oil to the water-repellent filter 60, which hinders gas flow through the intercommunicating holes 58 (introduction of air from outside the oxygen sensor or ejection of the exhaust gas which has entered the interior of the oxygen sensor), can be reduced.

Since the resin tube 50 is bendable, the resin tube 50 can be disposed along the route of the lead wires 13–16. Specifically, the length of the resin tube 50 can be increased so long as an ambient space around the installed oxygen sensor permits. Thus, in the case where the oxygen sensor is attached to an exhaust pipe, heat transmitted from the metallic shell 29 to the rubber member 54 through the resin tube 50 can be decreased. As a result, a temperature rise of the rubber member 54 and the water-repellent filter 60 can be suppressed, thereby extending their service lives and thus extending the service life of the oxygen sensor.

The resin tube 50 is attached to the metallic shell 29 by means of the metallic internal and external cylindrical members 33 and 39, which are disposed opposite the flow path with respect to the metallic shell 29. Thus, a temperature rise of the resin tube 50 is suppressed, thereby extending its service life. Since the resin tube 50 formed from a fluorine-containing resin serves as the second cover, the total weight of the oxygen sensor can be decreased as compared to the case where the second cover is formed from a metal. Also, the elasticity of the second cover facilitates maintenance of a seal at a connection with the external cylindrical member 39 serving as the first cover. Since a fluorine-containing resin is lower in thermal conductivity than a metal, a temperature rise of the rubber member 54 and the water-repellent filter 60 can be further suppressed, thereby extending their service lives.

Since the sheeted water-repellent filter 60 covers the side openings 58a of the intercommunicating holes 58 formed in the rubber member 54, good intercommunication is established; specifically, air can be reliably introduced into the interior of the gas sensor, and an exhaust gas which has entered the interior of the gas sensor can be reliably ejected to the exterior of the gas sensor.

While the present invention has been described with reference to the embodiment, the present invention is not limited thereto, but may be embodied in various other specific forms.

For example, the above embodiment is described while mentioning an oxygen sensor as a gas sensor. However, the present invention is not limited thereto. The present invention may be applied to, for example, NOx (nitrogen oxide) sensors and HC (hydrocarbon) sensors.

The above embodiment is described while mentioning the resin tube 50 of a fluorine-containing resin serving as the bendable second cover. However, the present invention is not limited thereto. The second cover may assume the form of cylindrical bellows made of a metal, thereby reliably protecting the lead wires 13–16 accommodated therein.

The application is based on Japanese Patent Application No. Hei. 11-174257 filed Jun. 21, 1999, which is incorporated herein by reference in its entirety.

What is claimed is:

1. A gas sensor for use in an environment exposing the gas sensor to oil splashing and/or heat, comprising:
   a detection element comprising an oxygen-ion-conductive solid electrolyte body and electrodes formed on the solid electrolyte body;
   a metallic shell formed so as to be attachable in a mounting hole formed in a wall of a flow path through which a gas to be measured flows, and adapted to hold the detection element;
   a cylindrical cover disposed at a side of the metallic shell opposite the flow path and adapted to introduce air to one of the electrodes formed on the solid electrolyte body, within which lead wires electrically connected to the electrodes of the detection element are disposed;
   an elastic member having an intercommunicating hole formed therein through which air is introduced into the interior of the cylindrical cover, and having through-holes formed therein through which the lead wires extend; and
   a water-repellent filter having gas permeability and positioned such that air to be introduced into the interior of the cylindrical cover through the intercommunicating hole formed in the elastic member passes therethrough, wherein a portion of the cylindrical cover is bendable to allow the elastic member to be moved to a position less exposed to oil splashing and/or heat.

2. The gas sensor as claimed in claim 1, wherein the cylindrical cover comprises:
   a first cover formed from a metal and disposed at a side of the metallic shell opposite the flow path; and
   a second cover which is bendable and disposed at a side of the first cover opposite the metallic shell.

3. The gas sensor as claimed in claim 2, wherein the second cover is formed from an elastic, heat-resistant resin or rubber.

4. The gas sensor as claimed in claim 1, wherein the water-repellent filter assumes the form of a sheet and is disposed so as to cover an opening of the intercommunicating hole facing the exterior of the gas sensor.

5. The gas sensor as claimed in claim 1, wherein the cylindrical cover comprises a resin tube and a caulking member, the elastic member is disposed within the resin tube so that an upper end of the resin tube overlaps the elastic member, and the caulking member is caulked at a portion of the gas sensor under which the resin tube and elastic member overlap so as to fixedly attach the elastic member to the upper end of the resin tube.

6. The gas sensor as claimed in claim 5, wherein the caulked portion is arranged at an end of the gas sensor opposite the flow path.

7. The gas sensor as claimed in claim 5, wherein the resin tube is bendable to move the elastic member to a position less exposed to oil splashing and/or heat.

8. The gas sensor as claimed in claim 1, wherein the cylindrical cover comprises a resin tube bendable to move the elastic member to a position less exposed to oil splashing and/or heat.

* * * * *